United States Patent
Fan et al.

(10) Patent No.: US 12,247,217 B2
(45) Date of Patent: Mar. 11, 2025

(54) METHOD FOR PREPARING 3D BRAIN ORGANOIDS

(71) Applicant: ZHEJIANG HUODE BIOENGINEERING COMPANY LIMITED, Hangzhou (CN)

(72) Inventors: Jing Fan, Hangzhou (CN); Anxin Wang, Hangzhou (CN); Tan Zou, Hangzhou (CN)

(73) Assignee: ZHEJIANG HUODE BIOENGINEERING COMPANY LIMITED, Hangzhou (CN)

( * ) Notice: Subject to any disclaimer, the term of this patent is extended or adjusted under 35 U.S.C. 154(b) by 836 days.

(21) Appl. No.: 16/979,981

(22) PCT Filed: Mar. 11, 2019

(86) PCT No.: PCT/CN2019/077595
§ 371 (c)(1),
(2) Date: Sep. 11, 2020

(87) PCT Pub. No.: WO2019/174535
PCT Pub. Date: Sep. 19, 2019

(65) Prior Publication Data
US 2021/0355438 A1    Nov. 18, 2021

(30) Foreign Application Priority Data

Mar. 14, 2018 (CN) .......................... 201810208751.0

(51) Int. Cl.
*C12N 5/079* (2010.01)
(52) U.S. Cl.
CPC ........ *C12N 5/0618* (2013.01); *C12N 2500/38* (2013.01); *C12N 2500/40* (2013.01); *C12N 2501/13* (2013.01); *C12N 2509/00* (2013.01); *C12N 2513/00* (2013.01); *C12N 2523/00* (2013.01); *C12N 2527/00* (2013.01)

(58) Field of Classification Search
CPC ............. C12N 5/0618; C12N 2500/38; C12N 2500/40; C12N 2501/13; C12N 2509/00; C12N 2513/00; C12N 2523/00; C12N 2527/00
See application file for complete search history.

(56) References Cited

U.S. PATENT DOCUMENTS

| | | | |
|---|---|---|---|
| 10,087,471 B2 | 10/2018 | Freed et al. | |
| 10,988,733 B2 * | 4/2021 | Shyu | A61K 35/545 |
| 11,724,460 B2 * | 8/2023 | Huang | B29C 64/00 |
| | | | 264/308 |
| 2015/0265652 A1 * | 9/2015 | George | A61P 25/16 |
| | | | 435/6.12 |
| 2018/0051248 A1 | 2/2018 | McMahon et al. | |

FOREIGN PATENT DOCUMENTS

| | | |
|---|---|---|
| CN | 104673752 A | 6/2015 |
| CN | 106834233 A | 6/2017 |
| CN | 108456659 A | 8/2018 |
| WO | WO2017/160234 A1 | 9/2017 |
| WO | WO2017160234 A | 9/2017 |
| WO | WO2018228948 A | 12/2018 |
| WO | WO2018232476 A1 | 12/2018 |

OTHER PUBLICATIONS

Lu, Y.C., et al., "Designing compartmentalized hydrogel microparticles for cell encapsulation and scalable 3D cell culture," Journal of Materials Chemistry B 3(3): 353-360. doi: 10.1039/c4tb01735h. Epub Dec. 4, 2014. (Year: 2014).*
Zhang, S. C., et al., "In vitro differentiation of transplantable neural precursors from human embryonic stem cells," Nature Biotechnology 19(12): 1129-1133. doi: 10.1038/nbt1201-1129. (Year: 2001).*
Aurora, M., "Cell Culture Media: A Review," Mater. Methods. 2013;3:175. doi.org/10.13070/mm.en.3.175. (Year: 2013).*
Montgomery, D. C., "Design and Analysis of Experiments," Eighth Edition. Arizona State University. Copyright 2013. (Year: 2013).*
Hughes, C. S., et al., "Matrigel: a complex protein mixture required for optimal growth of cell culture," Proteomics 10(9): 1886-1890. doi: 10.1002/pmic.200900758. (Year: 2010).*
Aisenbrey, E. A., and Murphy, W. L., "Synthetic alternatives to Matrigel," Nat Rev Mater 5(7): 539-551. doi: 10.1038/s41578-020-0199-8. (Year: 2020).*
Chen, Y., et al., "NS21: re-defined and modified supplement B27 for neuronal cultures," J Neurosci Methods 171(2): 239-247. doi: 10.1016/j.jneumeth.2008.03.013. (Year: 2008).*
Eiraku M et al., "Self-organized formation of polarized cortical tissues from ESCs and its active manipulation by extrinsic signals", *Cell Stem Cell*. 2008;3(5):519-532.

(Continued)

*Primary Examiner* — Tracy Vivlemore
*Assistant Examiner* — Eric J Rogers
(74) *Attorney, Agent, or Firm* — FINNEGAN, HENDERSON, FARABOW, GARRETT & DUNNER, LLP

(57) ABSTRACT

The present invention provides a method for preparing 3D brain organoids, comprising the following steps: neurospheres obtained by the RONA method are dissociated into single cells by accutase, plated on a cell culture plate after being counted, cultured in medium A until day 7; neurospheres are cultured in medium B until day 25~35, and then they are encapsulated by Matrigel; neurospheres are further cultured in media B until day 55~65, and then they are encapsulated by Matrigel for the second time and cultured continually afterwards. The present invention also provides a medium for culturing 3D brain organoids. The present invention begins with highly purified neurospheres obtained by the RONA method, and neuronal stem cells can be controlled and cultured to achieve true 3D brain organoids with uniform size and structure by this relatively simple method. The 3D brain organoids have six-layered cortical structure of the brain and various subtypes of inhibitory interneuron cells, which are suitable for disease research in vitro, drug screening, etc., and are of great significance in industrialization.

6 Claims, 5 Drawing Sheets

(56) References Cited

OTHER PUBLICATIONS

Paşca AM et al., "Functional cortical neurons and astrocytes from human pluripotent stem cells in 3D culture", *Nat Methods.*, 2015;12(7):671-678.
Jo J et al., "Midbrain-like Organoids from Human Pluripotent Stem Cells Contain Functional Dopaminergic and Neuromelanin-Producing Neurons", *Cell Stem Cell*, 2016; 19:248-257.
Extended European Search Report for EP19768309.7, dated Apr. 12, 2021.
Wachs FP et al., "High efficacy of clonal growth and expansion of adult neural stem cells", *Lab Invest.*, Jul. 2003;83(7):949-62.
Xu JC et al., "Cultured networks of excitatory projection neurons and inhibitory interneurons for studying human cortical neurotoxicity", *Sci Transl Med.*, Apr. 6, 2016; 8(333): 333ra48.
Lancaster et al., Cerebral organoids model human brain development and microcephaly, *Nature*, 2013, vol. 501, p. 7467.
Lancaster et al., Generation of cerebral organoids from human pluripotent stem cells, *Nature Protoc.* 2014, vol. 9, p. 2329.
Lee et al., CYP3A5 Mediates Effects of Cocaine on Human Neocorticogenesis: Studies using an In Vitro 3D Self-Organized hPSC Model with a Single Cortex-Like Unit, *Neuropsychopharmacology*, 2017, vol. 42, p. 774-784.
Qian et al., Brain Region-specific Organoids using Mini-bioreactors for Modeling ZIKV Exposure, *Cell*, 2016, vol. 165, p. 1238-1254.
Xu et al., Cultured networks of excitatory projection neurons and inhibitory interneurons for studying human cortical neurotoxicity, *Sci. Trans. Med.* vol. 8, p. 333ra48.
International Search Report for International Application No. PCT/CN2019/077595, dated Jun. 11, 2019.
Written Opinion for International Application No. PCT/CN2019/077595, dated Jun. 11, 2019.
BD Biosciences, "BD Matrigel® Matrix," 2011, 7 pages.
Brewer et al., "Optimized survival of hippocampal neurons in B27-supplemented Neurobasal, a new serum-free medium combination," J Neurosci Res, Aug. 1, 1993, 35(5):567-576.

\* cited by examiner

METHOD FOR PREPARING 3D BRAIN ORGANOIDS

This application is a national stage filing under 35 U.S.C. § 371 of International Application No. PCT/CN2019/077595, filed on Mar. 11, 2019, which claims the benefit of the filing date of Chinese Patent Application No. 201810208751.0, filed on Mar. 14, 2018.

FIELD OF THE INVENTION

The present invention belongs to the technical field of 3D brain organoids, and particularly relates to a method of preparing 3D brain organoids from human neurospheres.

BACKGROUND OF THE INVENTION

Human neuronal stem cells or brain tissues are difficult to obtain and can hardly be cultured in vitro, making neurological research and drug developments stagnated since no good humanized model is available. Human neuronal stem cells obtained by embryonic stem cells or induced pluripotent stem cells have been used as a neurological disease model, which is an international innovation and hotspot in recent years. Meanwhile, 3D culture not only can simulate brain tissue environment and cell communication, but also plays an important role in promoting the maturation and function of neurons. Moreover, the role of 3D brain organoids in the study of human brain development and related diseases is irreplaceable. Recently, in vitro culture of various human 3D organoids has become a new hot spot.

The traditional method of preparing human 3D brain organoids generally starts from the embryonic body, for example, preparation method of 3D brain organoids published in *Nature* and *Nature Protocol* in 2013 and 2014 by Lancaster et al. has made a big step forward in utilization of human pluripotent stem cells (including embryonic stem cells and induced pluripotent stem cells) in vitro to obtain 3D simulation of human brain organs. Recently, similar method published in *Cell* (2016) by Qian et al. has been applied to study the mechanism of Zika virus-induced cerebellar disease by preparing brain organoids from human pluripotent stem cells, and a small multi-well plate with stirring device has been invented to reduce the amount and cost of the factor as well as to improve the homogeneity. However, it is difficult to control the repeatability and structural similarity of the products steadily because the 3D brain organoids obtained by these two methods may contain cells and structures of other embryonic layers, and therefore applications in the field of neurological disease models and drug screening are limited, the representativeness and reliability of the obtained data are also affected.

As published in *Neuropsychopharmacology* in 2017 by Lee et al., rose-like cell clusters (mainly NPC, neural precursor cells) with the size of 50,000-200,000 mm are picked manually and induced. However, the obtained 3D new cerebral cortex has no potentials of developing into the hindbrain (negative NKX2.1 staining). In addition, this method is too complicated; meanwhile, simplicity, mass production as well as uniformity can't be achieved.

DESCRIPTION OF THE INVENTION

In view of the above, the object of the present invention is to provide a method for preparing 3D brain organoids. The 3D brain organoids with uniform size and structure can be obtained by this method, which is simple and suitable for industrialization.

The present invention provides a method for preparation of 3D brain organoids, comprising the following steps:

The neurospheres obtained by the RONA method are firstly dissociated into single cells by accutase; cells are plated on a cell culture plate after being counted, cultured in medium A until day 7; neurospheres are cultured in medium B until day 25-35, and then the neurospheres are encapsulated; when neurospheres are cultured in media B until day 55-65, they are encapsulated for the second time and cultured continually afterwards.

The mentioned medium A comprises: retinoic acid, BDNF, GDNF, ascorbic acid, cAMP, Neurobasal medium and B-27® supplement (Vitamin A free);

The mentioned medium B comprises: BDNF, GDNF, ascorbic acid, cAMP, Neurobasal medium and B-27® supplement (Vitamin A free).

MATRIGEL® is a commercially available solubilized basement membrane preparation extracted from Engelberth-Holm-Swarm (EHS) mouse sarcoma tumors for use in making reconstituted basement membrane hydrogels for cell culture applications (Hughes et al., Proteomics, 2010, 10(9): 1886-1890). MATRIGEL® comprises approximately 60% laminin, 30% collagen IV, and 8% entactin, and further contains heparan sulfate proteoglycan (perlecan), transforming growth factor (TGF-beta), epidermal growth factor (EGF), insulin-like growth factor (IGF-1), basic fibroblast growth factor (bFGF), tissue plasminogen activator, platelet-derived growth factor (PDGF), nerve growth factor (NGF), and vascular endothelial growth factor (VEGF) (BD MATRIGEL® Matrix Frequently Asked Questions, 2011).

B-27® supplement is a commercially available neuronal cell culture supplement comprising bovine serum albumin (BSA), catalase, glutathione (reduced), insulin, superoxide dismutase, transferrin, triiodo-I-thyronine (T3), L-carnitine, ethanolamine, D-galactose, putrescine, selenium, corticosterone, linoleic acid, linolenic acid, progesterone, DL-alpha-tocopherol (vitamin E), DL-alpha-tocopherol acetate, biotin, and retinyl acetate (vitamin A) (Brewer et al., *J Neurosci Res*, 1993, 35(5):567-576). B-27® supplement without Vitamin A, i.e., "B-27® supplement (Vitamin A-free)," may also be used in the present invention.

The present invention begins with highly purified neurospheres obtained by the RONA method, guarantying that more than 99% cells are neural stem cells, and thus problems existing in other methods, such as containing non-neuronal stem cells and non-brain tissue in subsequent cultures, can be well solved. According to the present invention, neurospheres are dissociated into single cells, which are plated in a fixed number after being counted, the uniformity of cell mass size and composition can be ensured, even though the size and structure of the 3D brain organoids will not be significantly different after 90 days' culture. Meanwhile, the medium A and the medium B used in the culture process of the present invention ensure that the cultured 3D brain organoids can be induced into the brain tissue of the forebrain, the midbrain and the hindbrain, as well as cells and structure of the six-layered brain cortex.

The present invention begins with highly purified neurospheres obtained by the RONA method, guarantying that more than 99% cells are neural stem cells. The specific process of purifying neurospheres by the RONA method is referred to the article "Cultured Networks of Excitatory Projection Neurons and Inhibitory Interneurons for Studying Human Cortical Neurotoxicity" published in *Science Translational Medicine* by Xu J C and Fan J in April, 2016.

In the present invention, the neurospheres purified by the RONA method are dissociated by accutase into single cells, which are plated on a cell culture plate after being counted. Specifically, the same number of 1000-50000 cells are plated on a multi-well cell culture plate to ensure uniformity of cell cluster size after being counted. In one embodiment, an equal number of 1000-10000 cells are plated on a 96-well cell culture plate with ultra-low attachment at the round bottom.

Neurospheres are cultured in medium A after being plated, and the mentioned medium A comprises: retinoic acid, BDNF, GDNF, ascorbic acid, cAMP, Neurobasal medium and B-27® supplement (Vitamin A free). In one embodiment, the mentioned medium A comprises: 1-5 µM retinoic acid, 10-30 ng/mL BDNF, 10-30 ng/mL GDNF, 0.1-0.5 mM ascorbic acid, 5-15 µM cAMP, Neurobasal and B-27® supplement (Vitamin A free). In one embodiment, the mentioned medium A comprises: 2 µM retinoic acid, 20 ng/mL BDNF, 20 ng/mL GDNF, 0.2 mM ascorbic acid, 10 µM cAMP, Neurobasal and B-27® supplement (Vitamin A free), wherein, the dosage ratio of Neurobasal and B-27® supplement (Vitamin A free) is 50:1.

Cells are cultured in medium A after being plated, shaken on the low-speed orbital shaker in a humidified incubator with 5% $CO_2$ at 37° C., and then half-medium changes are performed every 3 to 5 days. It can be observed that neurospheres with uniform size are formed in each well on day 2. Neurospheres are cultured in medium A until day 7, and then neurospheres are transferred into medium B and cultured under the same culturing conditions.

In the present invention, the mentioned medium B comprises: BDNF, GDNF, ascorbic acid, cAMP, Neurobasal medium and B-27® supplement (Vitamin A free). In one embodiment, the mentioned medium B comprises: 10-30 ng/mL BDNF, 10-30 ng/mL GDNF, 0.1-0.5 mM ascorbic acid, 5-15 µM cAMP, Neurobasal and B-27® supplement (Vitamin A free). In one embodiment, the mentioned medium B comprises: 20 ng/mL BDNF, 20 ng/mL GDNF, 0.2 mM ascorbic acid, 10 µM cAMP, B-27® supplement (Vitamin A free), wherein, the dosage ratio of Neurobasal and B-27® supplement (Vitamin A free) is 50:1.

Neurospheres are cultured in medium B until day 25-35, and then they are encapsulated; when neurospheres are cultured in media B until day 55-65, they are encapsulated for the second time and cultured continually afterwards. Homogeneous 3D organoids with simulated human brain composition can be obtained, and further encapsulation and culture can be done depending on the requirements.

Specifically, in the present invention, neurospheres are cultured until day 25-35, and then they are encapsulated by MATRIGEL®; neurospheres are encapsulated by MATRIGEL® for the second time when they are cultured until day 55-65, and cultured continually afterwards.

Specifically, in the present invention, the method for preparation further comprises the following steps: neurospheres are encapsulated for the third time when they are cultured until day 85-100, and cultured continually afterwards.

Specifically, in the present invention, neurospheres are encapsulated by using MATRIGEL® for the third time when they are cultured until day 85-100, and cultured continually afterwards.

In one embodiment of the present invention, neurospheres are encapsulated when they are cultured until day 30, and neurospheres are encapsulated for the second time when they are cultured until day 60. Neurospheres are encapsulated for the third time when they are cultured until day 90, and cultured continually afterwards.

The experimental results indicate that the present invention begins with highly purified neurospheres obtained by the RONA method, and 3D cerebral corpuscles with relatively uniform size and structure can be obtained. The 3D cerebral corpuscles can reach up to 4 mm in diameter on day 88 and continue to grow; meanwhile, markers such as Nestin, Tuj1, Foxg1, TBR2 and NKX2.1, etc. can be expressed in 3D cerebral corpuscles which are capable of developing into protocerebrum, deutocerebrum and tritocerebrum; in addition, 3D cerebral corpuscles can also express markers including BRN2, SATB2, CTIP2 and TBR1 with similar distribution and proportion as makers in the brain, and have the capacity to stably obtain the cerebral cortex structure.

The present invention begins with highly purified neurospheres obtained by the RONA method, and neuronal stem cells can be controlled as well as cultured to achieve true 3D brain organoids with uniform size and structure by this relatively simple method. The 3D brain organoids have six-layered cortical structure of the brain and various subtypes of inhibitory interneuron cells, which are suitable for disease research in vitro, drug screening, etc., and are of great significance in industrialization.

DESCRIPTION OF THE DRAWINGS

In order to illustrate embodiments of the present invention or technical solutions of the existing technology more clearly, the drawings used in the description of embodiments or the existing technology will be briefly introduced. Obviously, the drawings in the following description only relates to the embodiments of the present invention. Other appended drawings can also be obtained by ordinary technicians in the field from the provided drawings of the present invention without making any creative efforts.

DETAILED DESCRIPTION OF CERTAIN EMBODIMENTS

The technical solutions in the embodiments of the present invention will be described clearly and completely herein-after. Obviously, only part of the embodiments of the present invention is involved herein. All other embodiments acquired by ordinary technicians in this field based on the embodiments of the present invention without making any creative efforts are within the scope of protection of the present invention.

Example 1

Figure 1:
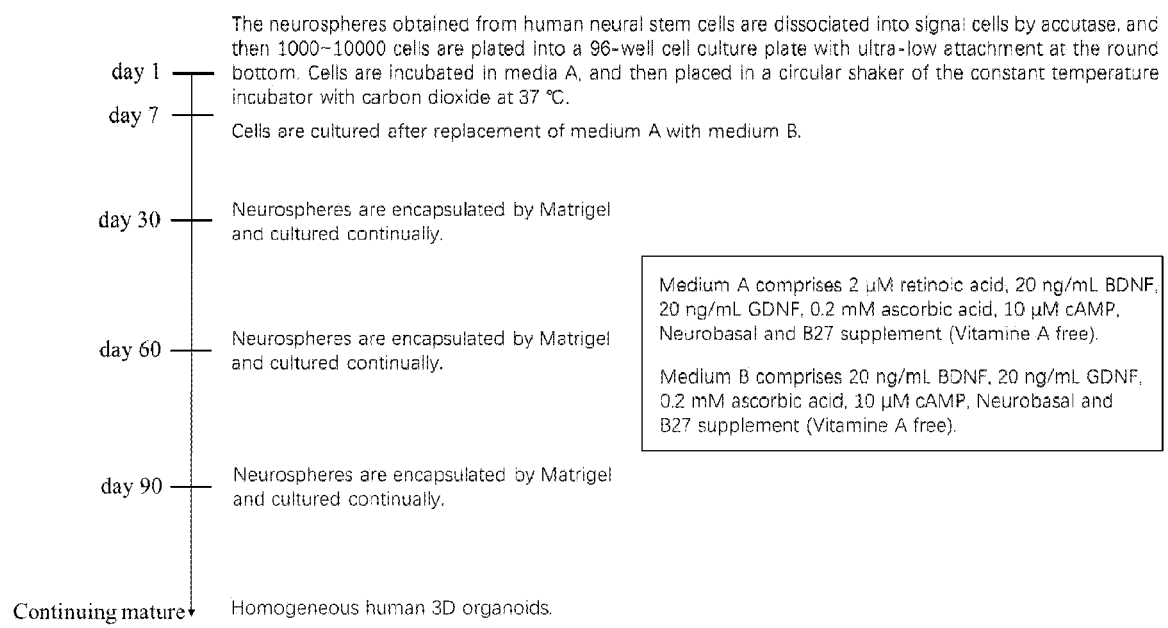
FIG. 1 is the flow chart of the preparation process of 3D brain organoids provided in example 1 of the present invention.
Figure 2:
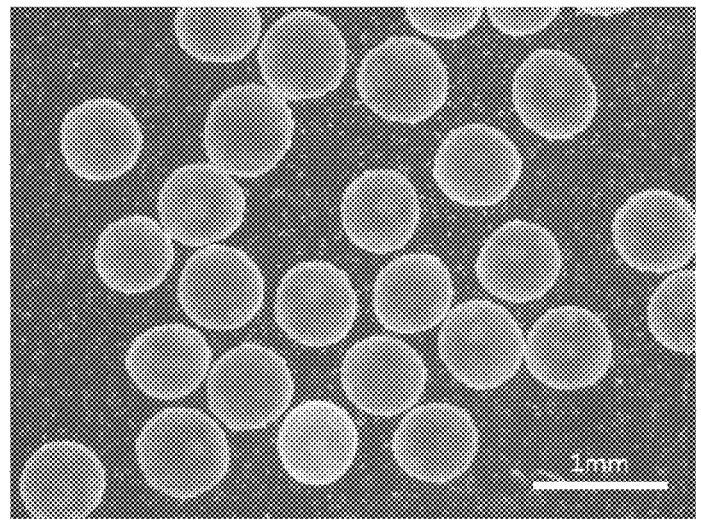
FIG. 2 is the image of 3D cerebral corpuscles cultured until day 17 provided in example 1 of the present invention.

FIG. 1 is a flow chart of the preparation process of 3D brain organoids provided in example 1 of the present invention.

Step 1: the neurospheres obtained by the RONA method (referring to "Cultured Networks of Excitatory Projection Neurons and Inhibitory Interneurons for Studying Human Cortical Neurotoxicity" published in *Science Translational Medicine* by Xu J C and Fan J in April, 2016) were dissociated into single cells by accutase, and then the same number of 5000 cells were plated on a 96-well cell culture plate with ultra-low attachment at the round bottom after cells were counted.

Cells were cultured in media A which was placed on the orbital shaker in a humidified incubator with 5% $CO_2$ at 37° C. for 7 days, and half-medium changes were performed every 3 to 5 days. Medium A comprised: 2 µM retinoic acid, 20 ng/ml BDNF and GDNF, 0.2 mM ascorbic acid, 10 µM cAMP of Neurobasal and B-27® supplement (Vitamin A free), wherein the dosage ratio of Neurobasal to B-27® supplement was 50:1.

Step 2: neurospheres with uniform size could be observed in each well on day 2. Medium A was replaced by media B on day 7. Neurospheres were cultured continually in medium B. Medium B comprised: 20 ng/mL BDNF and GDNF, 0.2 mM ascorbic acid, 10 µM cAMP of Neurobasal and B-27® supplement (Vitamin A free), wherein the dosage ratio of Neurobasal to B-27® supplement was 50:1.

Step 3: neurospheres were cultured in Media B until day 30, and then they were encapsulated by MATRIGEL® on the surface of non-hydrophilic sterile materials. Neurospheres were cultured on a 96-well culture plate until day 60, and then they were encapsulated by MATRIGEL® for the second time. Neurospheres were cultured in media B until day 90, homogeneous 3D organoids with simulated human brain composition could be obtained, and further encapsulation and culture can be made depending on the requirements.

Figure 3:
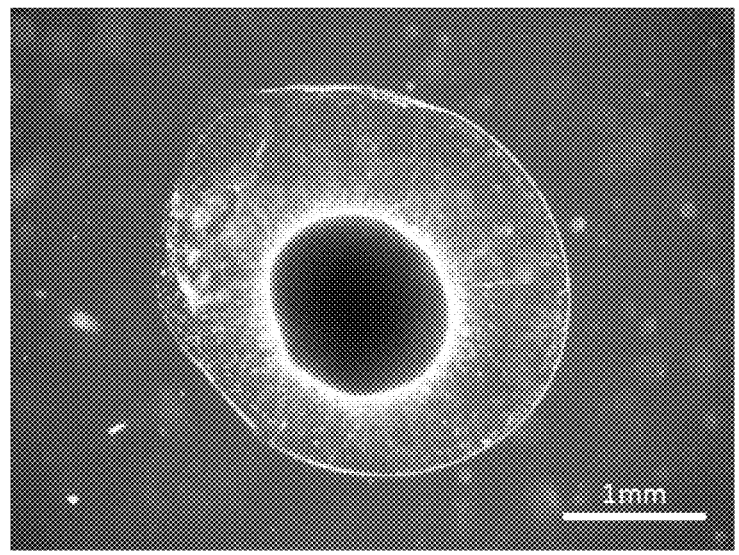
FIG. 3 is the image of 3D cerebral corpuscles cultured until day 50 provided in example 1 of the present invention.
Figure 4:
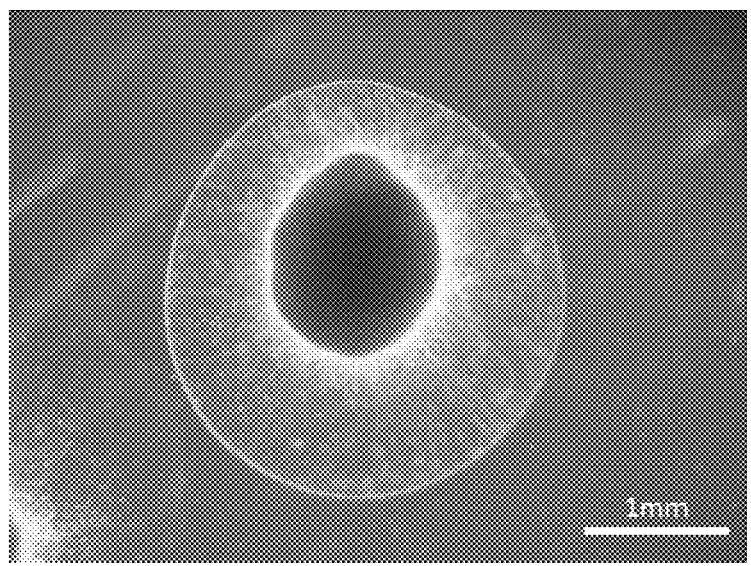
FIG. 4 is the image of 3D cerebral corpuscles cultured until day 50 provided in example 1 of the present invention.
Figure 5:
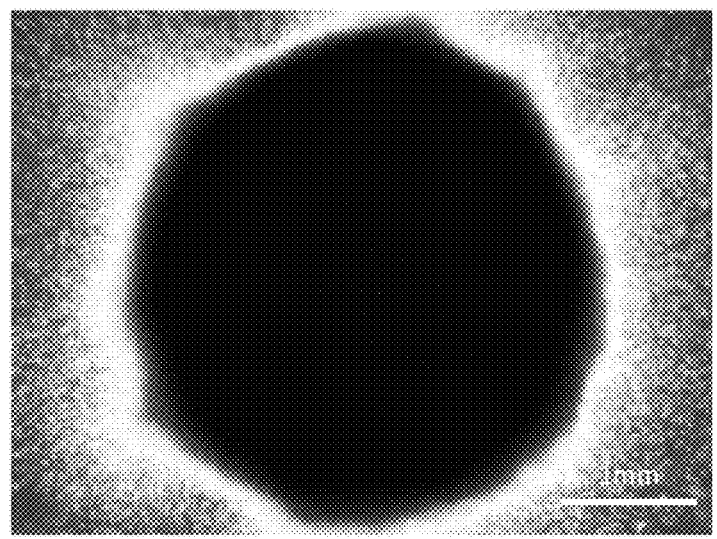
FIG. 5 is the image of 3D cerebral corpuscles cultured until day 88 provided in example 1 of the present invention.

Referring to FIG. 2, FIG. 3, FIG. 4 and FIG. 5, FIG. 2 shows the image of 3D cerebral corpuscles cultured until day 17 provided in example 1 of the present invention. FIG. 3 is the image of 3D cerebral corpuscles cultured until day 50 provided in example 1 of the present invention. FIG. 4 is the image of 3D cerebral corpuscles cultured until day 50 provided in example 1 of the present invention. FIG. 5 is the image of 3D cerebral corpuscles cultured until day 88 provided in example 1 of the present invention. As can be seen from FIG. 2 to FIG. 5, 3D cerebral corpuscles were relatively uniform in size and shape, could reach up to 4 mm in diameter on day 88, and continue to grow. However, the 3D cerebral corpuscles obtained by most of other methods are hard to grow up to such a size and remain healthy within the same time duration.

Figure 6:
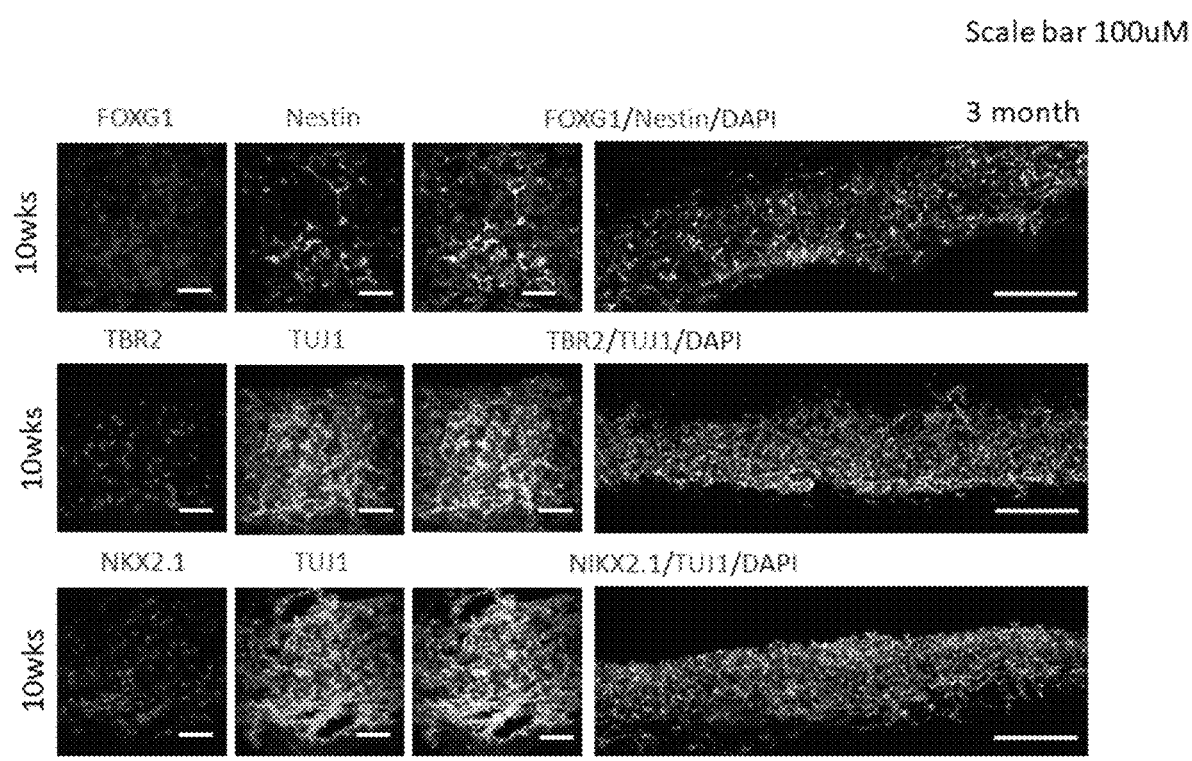
FIG. 6 shows tissue biopsies and staining images of progenitor cells from different brain regions of 3D cerebral corpuscles cultured until week 10.

Referring to FIG. 6, FIG. 6 shows tissue biopsies and staining images of progenitor cells from different brain regions of 3D cerebral corpuscles cultured until week 10. Among them, Nestin is a common marker protein expressed by neural precursor cells. Tuj1 is a protein marker commonly expressed by nerve cells. Foxg1 is a marker of forebrain precursor cells. TBR2 is a marker of mid-brain subventricalzone and neural precursor cells of hippocampus. NKX2.1 is a marker of hindbrain precursor cells and DAPI is a DNA dye. As shown in the FIG. 6, the 3D cerebral corpuscles obtained by the method of the present invention are capable of developing into the forebrain, the midbrain and the hindbrain.

Figure 7:
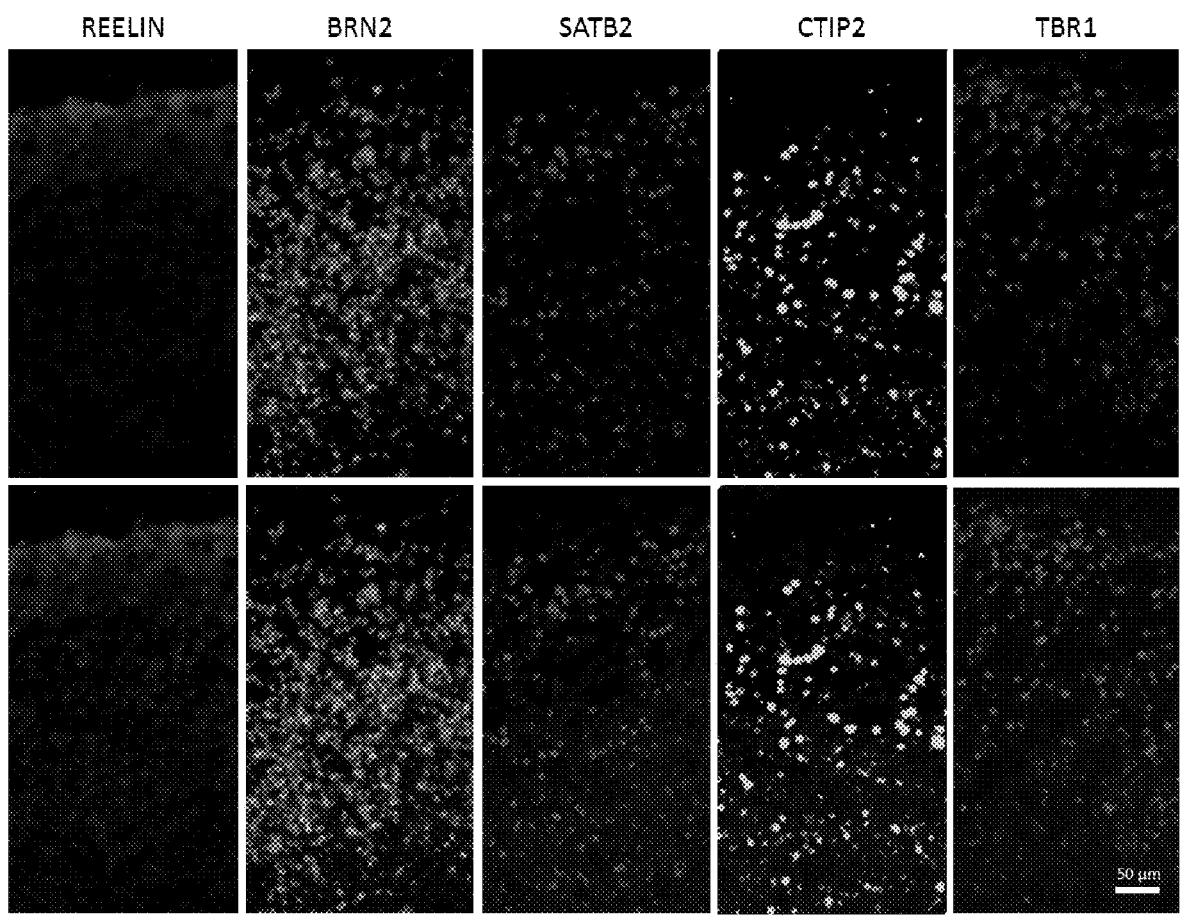
FIG. 7 shows tissue biopsies and staining images of neutrons from different cerebral cortex of 3D cerebral corpuscles cultured until day 88.

Referring to FIG. 7, FIG. 7 shows tissue biopsies and staining images of neutrons from different cerebral cortex of 3D cerebral corpuscle cultured until day 88. Among them, REELIN, BRN2, SATB2, CTIP2, and TBR1 are markers of neurons from the cerebral cortex I/II, III, IV, V, and VI, respectively. As can be seen from FIG. 7, the 3D brain corpuscles obtained by the method of the present invention can express markers of the above mentioned different cortices.

Figure 8:
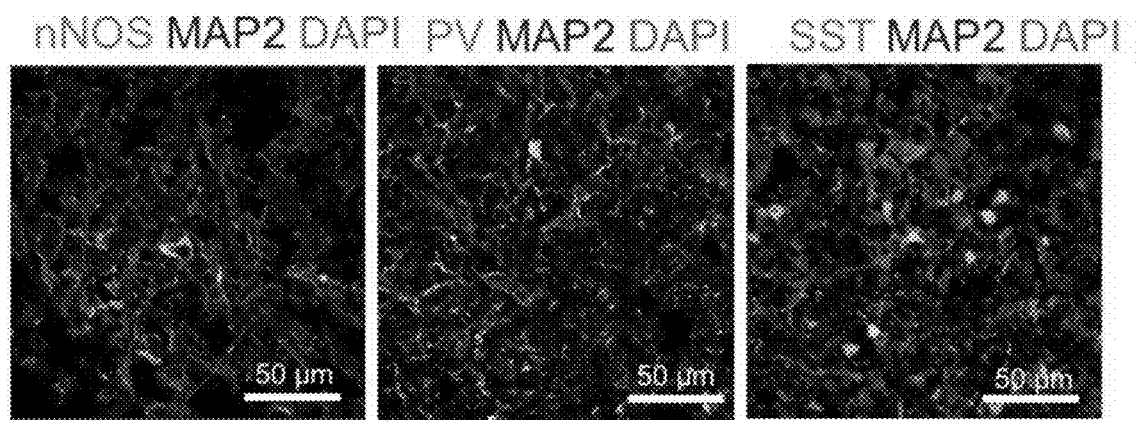
FIG. 8 shows tissue biopsies and staining images of glial cells and neurons of 3D cerebral corpuscles cultured until day 63.

Referring to FIG. 8, FIG. 8 shows tissue biopsies and staining images of glial cells and neurons of 3D cerebral corpuscle cultured until day 63. Among them, nNOS, PV and SST are markers of inhibitory brain neurons. MAP2 is a marker of relatively mature nerve cells, and DAPI is a DNA dye. As shown in the FIG. 8, the 3D cerebral corpuscles obtained by the method of the present invention at least contain such three inhibitory brain neurons, which play an important role in brain development and function, and the 3D cerebral corpuscles are relatively mature.

Figure 9:
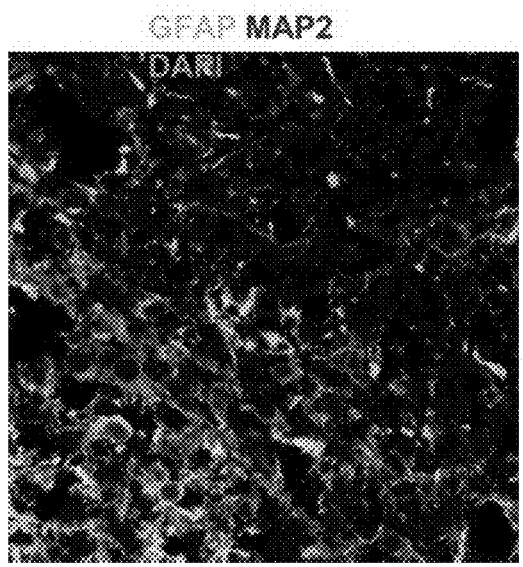
FIG. 9 shows tissue biopsies and staining image of glial cells and neurons of 3D cerebral corpuscles cultured until day 63.

According to statistics, the proportion of glial cells in all cells of 3D cerebral corpuscles is about 50-70%. As shown in the FIG. 9, 3D cerebral corpuscles obtained by the method described in the present invention contain glial cells which play an important role in brain development and function, and their proportion and distribution are very close to those of the human brain.

The above described examples are only preferred embodiments of the present invention. It should be pointed out that for ordinary technicians in the technical field, improvements and embellishments can be made without departing from the scope of the principles of the present invention, and these improvements and embellishments shall also be regarded as the scope of protection of the present invention.

The invention claimed is:

1. A method for preparation of 3D brain organoids comprising:
    (a) deriving a first batch of neurospheres from rosette neural aggregates (RONAs);
    (b) dissociating the first batch of neurospheres into single cells;
    (c) counting the single cells;
    (d) plated the single cells on a cell culture plate;
    (e) culturing the plated single cells in medium A for 7 days to obtain a second batch of neurospheres;
    (f) culturing the second batch of neurospheres in medium B until day 25-35;
    (g) encapsulating the second batch of neurospheres in a solubilized basement membrane preparation;
    (h) further culturing the encapsulated second batch of neurospheres in medium B until day 55-65; and
    (i) encapsulating the further cultured encapsulated second batch of neurospheres for a second time in the solubilized basement membrane preparation; and
    (j) continuously culturing the encapsulated second batch of neurospheres following the second encapsulation in the solubilized basement membrane preparation;
    wherein the medium A comprises: retinoic acid, BDNF, GDNF, ascorbic acid, cAMP, Neurobasal medium, and a neuronal cell culture supplement; and wherein the medium B comprises: BDNF, GDNF, ascorbic acid, cAMP, Neurobasal medium, and the neuronal cell culture supplement.

2. The method for preparation according to claim 1, wherein substantially the same number of the single cells are plated on each well in a multi-well cell culture plate; and wherein the number of the single cells plated on each well ranges from 1000 to 50000.

3. The method for preparation according to claim 1, wherein the medium A comprises: 1-5 μM retinoic acid, 10-30 ng/mL BDNF, 10-30 ng/mL GDNF, 0.1-0.5 mM ascorbic acid, 5-15 μM cAMP, Neurobasal medium, and the neuronal cell culture supplement;

wherein the medium B comprises: 10-30 ng/mL BDNF, 10-30 ng/mL GDNF, 0.1-0.5 mM ascorbic acid, 5-15 μM cAMP, Neurobasal medium, and the neuronal cell culture supplement; and wherein the neuronal cell culture supplement is Vitamin A-free.

4. The method for preparation according to claim 3, wherein the medium A comprises: 2 μM retinoic acid, 20 ng/mL BDNF, 20 ng/mL GDNF, 0.2 mM ascorbic acid, 10 μM cAMP, Neurobasal medium, and the neuronal cell culture supplement;

wherein the medium B comprises: 20 ng/mL BDNF, 20 ng/mL GDNF, 0.2 mM ascorbic acid, 10 μM cAMP, Neurobasal medium, and the neuronal cell culture supplement; and wherein the neuronal cell culture supplement is Vitamin A-free.

5. The method for preparation according to claim 1, comprising:
   (k) further culturing the encapsulated second batch of neurospheres following the second encapsulation in medium B until day 85-100;
   (l) encapsulating the further cultured encapsulated second batch of neurospheres for a third time in the solubilized basement membrane preparation; and
   (m) continuously culturing the second batch of neurospheres following the third encapsulation in the solubilized basement membrane preparation.

6. The method for preparation according to claim 5, wherein in step (f), the second batch of neurospheres are cultured until day 30; in step (h), the encapsulated second batch of neurospheres are cultured until day 60; and in step (k), the encapsulated second batch of neurospheres following the second encapsulation in the solubilized basement membrane preparation are cultured until day 90.

\* \* \* \* \*